United States Patent
Shener-Irmakoglu

(10) Patent No.: US 11,666,354 B2
(45) Date of Patent: *Jun. 6, 2023

(54) TISSUE RESECTION SYSTEM

(71) Applicant: Covidien LP, Mansfield, MA (US)

(72) Inventor: Cemal Shener-Irmakoglu, Hot Springs, AR (US)

(73) Assignee: Covidien LP, Mansfield, MA (US)

( * ) Notice: Subject to any disclaimer, the term of this patent is extended or adjusted under 35 U.S.C. 154(b) by 177 days.

This patent is subject to a terminal disclaimer.

(21) Appl. No.: 16/998,038

(22) Filed: Aug. 20, 2020

(65) Prior Publication Data

US 2020/0375624 A1    Dec. 3, 2020

Related U.S. Application Data

(63) Continuation of application No. 15/544,985, filed as application No. PCT/US2015/013356 on Jan. 28, 2015, now Pat. No. 10,772,652.

(51) Int. Cl.
*A61B 17/32*    (2006.01)
*A61B 1/00*    (2006.01)
(Continued)

(52) U.S. Cl.
CPC .. *A61B 17/320016* (2013.01); *A61B 1/00068* (2013.01); *A61B 1/015* (2013.01);
(Continued)

(58) Field of Classification Search
CPC ......... A61B 1/012; A61B 1/015; A61B 1/018; A61B 1/303; A61B 1/307; A61B 1/317;
(Continued)

(56) References Cited

U.S. PATENT DOCUMENTS 1,585,934 A    5/1926 Muir
1,666,332 A    4/1928 Hirsch
(Continued)

FOREIGN PATENT DOCUMENTS

DE    3206381 A1    9/1983
DE    3339322 A1    5/1984
(Continued)

*Primary Examiner* — Ryan N Henderson
(74) *Attorney, Agent, or Firm* — Carter, DeLuca & Farrell LLP

(57) ABSTRACT

A surgical system can include a first instrument defining a first channel and a second instrument receivable by the first channel. The second instrument can include a second channel. A valve coupled to the first instrument controls fluid flow through the first channel. The valve has at least two positions and in one position, the impedance of fluid flow through the valve into the first channel (when the second instrument is not received in the first channel) is substantially the same as when the valve is the other position and the first channel partially blocked by the second instrument. In another aspect, a surgical system can include an outer member and the first instrument can be received within the outer member to define a second channel there between. The first instrument can include a visualization system and an illumination system.

17 Claims, 16 Drawing Sheets

(51) Int. Cl.
  *A61B 1/015* (2006.01)
  *A61M 31/00* (2006.01)
  *A61B 1/018* (2006.01)
  *A61B 1/303* (2006.01)
  *A61M 3/02* (2006.01)
  *A61B 17/00* (2006.01)
  *A61B 17/42* (2006.01)
  *A61M 39/24* (2006.01)

(52) U.S. Cl.
  CPC .............. *A61B 1/018* (2013.01); *A61B 1/303* (2013.01); *A61M 3/0229* (2013.01); *A61M 31/00* (2013.01); *A61B 2017/0034* (2013.01); *A61B 2017/4216* (2013.01); *A61B 2217/005* (2013.01); *A61B 2217/007* (2013.01); *A61M 2039/2473* (2013.01); *A61M 2205/3334* (2013.01); *A61M 2205/70* (2013.01); *A61M 2210/1433* (2013.01)

(58) Field of Classification Search
  CPC ....... A61B 1/00094; A61B 1/12; A61B 1/126; A61B 1/127; A61B 1/128; A61B 1/00068; A61B 1/00119; A61B 1/00128; A61B 2017/320016; A61B 2017/32002; A61B 2017/320024; A61B 2017/320028; A61B 2017/320032; A61M 39/22; A61M 39/223; A61M 39/24; A61M 2039/224; A61M 2039/2473; A61M 2039/248; A61M 2039/2486
  See application file for complete search history.

(56) References Cited

U.S. PATENT DOCUMENTS

| | | |
|---|---|---|
| 1,831,786 A | 11/1931 | Duncan |
| 2,708,437 A | 5/1955 | Hutchins |
| 3,297,022 A | 1/1967 | Wallace |
| 3,686,706 A | 8/1972 | Finley |
| 3,734,099 A | 5/1973 | Bender et al. |
| 3,791,379 A * | 2/1974 | Storz .................. A61B 1/12 137/625.24 |
| 3,812,855 A | 5/1974 | Banko |
| 3,835,842 A | 9/1974 | Iglesias |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,284 A | 7/1986 | Arakawa et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,409,453 A | 4/1995 | Lundquist et al. |
| 5,411,513 A | 5/1995 | Ireland et al. |
| 5,421,819 A | 6/1995 | Edwards et al. |
| 5,425,376 A | 6/1995 | Banys et al. |
| 5,429,601 A | 7/1995 | Conley et al. |
| 5,435,805 A | 7/1995 | Edwards et al. |
| 5,443,476 A | 8/1995 | Shapiro |
| 5,449,356 A | 9/1995 | Walbrink et al. |
| 5,456,673 A | 10/1995 | Ziegler et al. |
| 5,456,689 A | 10/1995 | Kresch et al. |
| 5,483,951 A | 1/1996 | Frassica et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |

(56) References Cited

U.S. PATENT DOCUMENTS

| | | |
|---|---|---|
| 5,575,756 A | 11/1996 | Karasawa et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1* | 7/2007 | Emanuel ............... A61B 1/12 606/15 |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,061,359 B2 | 11/2011 | Emanuel |
| 8,062,214 B2 | 11/2011 | Shener et al. |
| 8,419,626 B2 | 4/2013 | Shener-Irmakoglu et al. |
| 8,663,264 B2 | 3/2014 | Cesarini et al. |
| 8,678,999 B2 | 3/2014 | Isaacson |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,125,550 B2 | 9/2015 | Shener-Irmakoglu et al. |
| 9,155,454 B2 | 10/2015 | Sahney et al. |
| 10,772,652 B2* | 9/2020 | Shener-Irmakoglu ..................... A61M 31/00 |
| 2001/0039963 A1 | 11/2001 | Spear et al. |
| 2001/0047183 A1 | 11/2001 | Privitera et al. |
| 2002/0058859 A1 | 5/2002 | Brommersma |
| 2002/0165427 A1 | 11/2002 | Yachia et al. |
| 2003/0050603 A1* | 3/2003 | Todd ............... A61B 17/3421 604/164.02 |
| 2003/0050638 A1 | 3/2003 | Yachia et al. |
| 2003/0078609 A1 | 4/2003 | Finlay et al. |
| 2003/0114875 A1 | 6/2003 | Sjostrom |
| 2004/0082915 A1* | 4/2004 | Kadan ............. A61B 1/00105 604/164.04 |
| 2004/0204671 A1 | 10/2004 | Stubbs et al. |
| 2005/0043690 A1 | 2/2005 | Todd |
| 2005/0085692 A1 | 4/2005 | Kiehn et al. |
| 2006/0036132 A1 | 2/2006 | Renner et al. |
| 2006/0047185 A1* | 3/2006 | Shener ................ A61B 1/015 600/156 |
| 2006/0241586 A1 | 10/2006 | Wilk |
| 2006/0293560 A1* | 12/2006 | Nguyen .................. A61F 6/06 600/104 |
| 2007/0238928 A1* | 10/2007 | Maseda ............ A61B 1/00137 600/153 |
| 2008/0015621 A1 | 1/2008 | Emanuel |
| 2008/0058588 A1 | 3/2008 | Emanuel |
| 2008/0058842 A1 | 3/2008 | Emanuel |
| 2008/0097468 A1 | 4/2008 | Adams et al. |
| 2008/0097469 A1 | 4/2008 | Gruber et al. |
| 2008/0097470 A1 | 4/2008 | Gruber |
| 2008/0097471 A1 | 4/2008 | Adams et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0245371 A1 | 10/2008 | Gruber |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262308 A1 | 10/2008 | Prestezog et al. |

(56) References Cited

U.S. PATENT DOCUMENTS

| | | | | |
|---|---|---|---|---|
| 2009/0088600 A1* | 4/2009 | Meloul | ................ | A61B 1/2676 600/154 |
| 2010/0087798 A1 | 4/2010 | Adams et al. | | |
| 2010/0152647 A1 | 6/2010 | Shener et al. | | |
| 2011/0166419 A1 | 7/2011 | Reif et al. | | |
| 2012/0078038 A1 | 3/2012 | Sahney et al. | | |
| 2013/0131452 A1 | 5/2013 | Kuroda et al. | | |
| 2014/0031834 A1 | 1/2014 | Germain et al. | | |
| 2019/0388162 A1* | 12/2019 | Azizian | ................ | A61B 34/37 |

FOREIGN PATENT DOCUMENTS

| | | |
|---|---|---|
| DE | 3601453 A1 | 9/1986 |
| DE | 3615694 A1 | 11/1987 |
| DE | 4038398 A1 | 6/1992 |
| DE | 4440035 A1 | 5/1996 |
| DE | 19633124 A1 | 5/1997 |
| DE | 19751632 C1 | 9/1999 |
| DE | 102006022827 A1 | 12/2006 |
| EP | 0310285 A2 | 4/1989 |
| EP | 0327410 A1 | 8/1989 |
| EP | 0557044 A1 | 8/1993 |
| EP | 0582295 A2 | 2/1994 |
| EP | 0606531 A2 | 7/1994 |
| EP | 0621008 A2 | 10/1994 |
| EP | 0806183 A1 | 11/1997 |
| EP | 1681022 A1 | 7/2006 |
| GB | 2093353 A | 9/1982 |
| GB | 2311468 A | 10/1997 |
| JP | H0175416 U | 5/1989 |
| JP | 2002529185 A | 9/2002 |
| JP | 2002538889 A | 11/2002 |
| JP | 2003245247 A | 9/2003 |
| NL | 1006944 C2 | 3/1999 |
| WO | 8101648 A1 | 6/1981 |
| WO | 9211816 A2 | 7/1992 |
| WO | 9307821 A1 | 4/1993 |
| WO | 9315664 A1 | 8/1993 |
| WO | 9426181 A1 | 11/1994 |
| WO | 9505777 A1 | 3/1995 |
| WO | 9510981 A1 | 4/1995 |
| WO | 9510982 A1 | 4/1995 |
| WO | 9522935 A1 | 8/1995 |
| WO | 9530377 A1 | 11/1995 |
| WO | 9611638 A1 | 4/1996 |
| WO | 9626676 A1 | 9/1996 |
| WO | 9709922 A1 | 3/1997 |
| WO | 9717027 A1 | 5/1997 |
| WO | 9719642 A1 | 6/1997 |
| WO | 9724071 A1 | 7/1997 |
| WO | 9734534 A1 | 9/1997 |
| WO | 9735522 A1 | 10/1997 |
| WO | 9809569 A1 | 3/1998 |
| WO | 9846147 A1 | 10/1998 |
| WO | 9903407 A1 | 1/1999 |
| WO | 9903409 A1 | 1/1999 |
| WO | 9907295 A1 | 2/1999 |
| WO | 9911184 A1 | 3/1999 |
| WO | 9939648 A1 | 8/1999 |
| WO | 9944506 A1 | 9/1999 |
| WO | 9960935 A1 | 12/1999 |
| WO | 9012010 A1 | 3/2000 |
| WO | 9028890 A1 | 5/2000 |
| WO | 0033743 A1 | 6/2000 |
| WO | 0044295 A1 | 8/2000 |
| WO | 0047116 A1 | 8/2000 |
| WO | 0057797 A1 | 10/2000 |
| WO | 0135831 A1 | 5/2001 |
| WO | 0158368 A1 | 8/2001 |
| WO | 0195810 A2 | 12/2001 |
| WO | 02069808 A2 | 9/2002 |
| WO | 03022164 A1 | 3/2003 |
| WO | 03077767 A1 | 9/2003 |
| WO | 2005060842 A1 | 7/2005 |
| WO | 2005096963 A2 | 10/2005 |
| WO | 2006105283 A2 | 10/2006 |
| WO | 2006121968 A2 | 11/2006 |
| WO | 2006121970 A2 | 11/2006 |
| WO | 2007044833 A2 | 4/2007 |
| WO | 2012044705 A1 | 4/2012 |

* cited by examiner

TISSUE RESECTION SYSTEM

CROSS REFERENCE TO RELATED APPLICATION

The present application is a continuation application of U.S. patent application Ser. No. 15/544,985, filed on Jul. 20, 2017, which is a U.S. National Stage Application under 35 U.S.C. § 371(a) of PCT/US2015/013356 filed Jan. 28, 2015, the entire contents of each of which are incorporated by reference herein.

FIELD OF THE INVENTION

This present disclosure relates to a tissue resecting system.

BACKGROUND

Endoscopic surgery of a distensible organ, such as a uterus, may be performed with an endoscope that is insertable into the uterus through the cervix and a resector or other tool that passes through the endoscope to cut or otherwise treat tissue in the uterus. During surgery, it often is desirable to distend the uterus with a fluid, such as saline, sorbitol, or glycine, in order provide a visible working space. Fluid can be infused into the uterus and removed from the uterus through the endoscope and/or the resector.

If the outflow of fluid from the uterus is greater than the inflow of fluid to the uterus, the uterus may collapse back to its normal state, making visualization of the uterus difficult. On the other hand, if the inflow of fluid is greater than the outflow of fluid such that the pressure created by the fluid is greater than the patient's mean arterial pressure, excess fluid can enter the patient's vascular system (known as intravasation), which can lead to serious complications or injury.

The proximal end of the endoscope can include an access port for the working channel into which the resector can be inserted enabling the distal cutting end of the resector to travel through the working channel and beyond the distal end of the endoscope in the uterus to cut or otherwise treat tissue in the uterus. The distention fluid also enters the uterus through the working channel of the endoscope.

The endoscope can be used in two modes, diagnostic mode and operative mode. In diagnostic mode, the endoscope can be used to view inside the uterus in order to identify tissue to be removed or otherwise treated. In diagnostic mode, no resector or other tool is present in the working channel, however distention fluid is driven into the uterus to facilitate observation and diagnosis. In operative mode, the resector or other tool is present in the working channel and impedes the flow of distention fluid through the working channel into the uterus. The insertion or removal of the resector or other tool from the working channel can cause disruptive or dangerous changes in the distention of the uterus.

To avoid this problem, U.S. Pat. Nos. 8,062,214 and 8,419,626 disclose the use of two valves at the access port of the endoscope that can be used to control the flow impedance of distention fluid into the working channel of the endoscope. The first valve can be an on/off valve that controls the flow of distention fluid into the working channel of the endoscope. The second valve can be a two position valve that controls the flow impedance into the working channel. When the second valve is in a first position, the access port is open permitting the resector or other tool can be inserted through the working channel. In addition, second valve can be configured whereby it also allows unimpeded flow of the distention fluid into the working channel where it is impeded by the resector or other tool in the working channel. When the second valve is in a second position, the access port is closed whereby the resector or other tool cannot be inserted into the working channel. However, in the second position, the second valve is configured to allow the distention fluid to flow through a smaller orifice that approximates the impedance produced when the resector or other tool is present in the working channel. As a result, the fluid impedance is substantially the same regardless of whether the resector or other tool is present in the working channel and the position of the second valve which helps to reduce the risks associated with larger changes in distention fluid pressure.

SUMMARY

To aid in addressing these issues, in an aspect of the present disclosure, a surgical system can include a first instrument having a fluid flow channel and a second instrument receivable by the first instrument fluid flow channel. The second instrument can include an aspiration channel. The system can include a valve coupled to the first instrument and configured to control fluid flow through the first instrument channel. The valve can be configured such that impedance of fluid flow through the first instrument channel can be substantially the same without the second instrument received in the first instrument channel and with the first instrument channel partially blocked by the second instrument such that the first instrument channel is limited to a region between the first and second instruments.

Embodiments of this aspect of the present disclosure may include one or more of the following features.

Embodiments of the present present disclosure can be directed to device, such as an endoscope, that can be used to control the distention fluid pressure using a single, multi-position valve. The device can include a working channel extending from a proximal end to a distal end that includes an access port at the proximal end. The access port can be adapted to receive a resector or other tool useful for endoscopic treatment of tissue adjacent the distal end of the device. The proximal end can include a fluidic connection enabling the device to be connected to a source of distention fluid that can be driven into the surgical site (e.g., a uterus) to distend the tissue in the area of the surgical site. A valve can be placed in the fluid path between the fluidic connection and the working channel to control the flow of distention fluid into the working channel.

The valve can have two or more operative positions for controlling the flow of distention fluid into the working channel. In a first position, the valve is open to unrestricted flow of distention fluid into the working channel. In a second position, the valve directs the flow of distention fluid through a flow restricted path into the working channel. The flow restricted path can be configured to produce the same flow impedance as when the resector or other tool is in the working channel. A third position can be provided wherein the valve is closed preventing distention fluid from flowing into the working channel.

In some embodiments, the first instrument can include an outer member and an inner member. The inner member can include a first instrument channel therethrough. The inner member can be received within the outer member, and the outer member and the inner member can define a second fluid flow channel therebetween. The second instrument can include a tube defining a second instrument channel therethrough. The tube partially blocks the first instrument fluid flow channel when received therein. The second fluid flow channel can have a cross-sectional area of, e.g., about 0.0083 to about 0.0249 square inches, preferably about 0.0166 square inches. The first instrument fluid flow channel can have a cross-sectional area of, e.g., about 0.0053 to about 0.0159 square inches, preferably about 0.0106 square inches. The second instrument channel can have a cross-sectional area of, e.g., about 0.0042 to about 0.013 square inches, preferably about 0.0085 square inches.

In some embodiments, the valve can include a housing and a body within the housing. The body defines a flow path therethrough and is moveable relative to the housing between a first position in which the fluid is directed to flow through a first flow path to the first instrument channel and a second position in which the fluid is directed to flow through a second flow path to the first instrument channel. In the first position, the tube of the second instrument tube partially blocks the first instrument fluid flow channel when received therein causing the fluid flow through the first instrument fluid flow channel to be impeded. In the second position, the first instrument fluid flow channel is not impeded by the tube of the second instrument, but the second flow path can be configured to impede fluid flow to the first instrument fluid flow channel such that the fluid flow is about that same as when the tube of the second instrument tube partially blocks the first instrument fluid flow channel. In accordance with some embodiments of the present disclosure, the impedance produced by the second flow path can be adjustable. In accordance with some embodiments of the present disclosure, the impedance produced by the second flow path can be changed by changing or replacing a structure of the second flow path.

The system can include a pump and the first instrument is configured to connect to the pump such that the pump infuses fluid through the first instrument channel. The pump can be programmed to infuse fluid through the first instrument channel to maintain a substantially constant pressure of between about 60 mm Hg and about 120 mm Hg inside a distensible organ. A sensor coupled to the pump can sense a flow impedance at a given flow rate, and a controller coupled to the sensor and the pump can compare the flow impedance to a predetermined flow impedance for the given flow rate to verify the identity of the first and second instruments.

The second instrument channel can be in fluid communication with a source of suction and a regulator can be interposed between the second instrument channel and the source of suction to regulate an amount of suction applied through the second instrument channel.

According to another aspect of the present disclosure, a method of regulating inflow through a valve includes positioning the valve in a first position directing the inflow along a path having a first impedance of flow into a working channel and positioning the valve in a second position directing the inflow along a path having a second impedance of flow into the working channel; and introducing a surgical instrument inserting the surgical instrument into the working channel. When the valve is in the first position and the surgical instrument is inserted into the working channel the impedance of flow into the working channel is about the same as the impedance of flow into the working channel when the valve is in the second position and the surgical instrument is removed from the working channel.

According to another aspect of the present disclosure, an apparatus for surgery can include an outer member and an inner member received within the outer member. The outer member and the inner member can define a first channel therebetween. The inner member can include an optical lens and can define a second channel for receiving a surgical instrument. The first and second channels can be configured such that a pump having an inflow rate of up to about 0.7 L/min connected to the second channel can maintain fluid pressure inside an organ.

Embodiments of this aspect can include one or more of the following features. A pump can be coupled to the second channel to introduce fluid through the second channel at an inflow rate up to about 0.7 L/min. The outer member can include a plurality of holes in fluid communication with the first channel. The plurality of holes can be positioned in a distal portion of the outer member. The second channel can include a D-shaped cross-section. The first channel can have a cross-sectional area, e.g., of about 0.0083 to about 0.0249 square inches, preferably about 0.0166 square inches. The second channel can have a cross-sectional area of, e.g., about 0.0053 to about 0.0159 square inches, preferably about 0.0106 square inches. The second channel can receive the surgical instrument therethrough. The surgical instrument can include a suction channel with a cross-sectional area of, e.g., about 0.0042 to about 0.013 square inches, preferably about 0.0085 square inches. A valve can be coupled to the inner member for regulating inflow through one of two or more pathways to the second channel such that inflow through a first pathway when the surgical instrument is received in the second channel has an impedance equal to the impedance through the second pathway when the surgical instrument is removed from the second channel.

According to another aspect of the present disclosure, a method includes infusing fluid into a distensible organ, and maintaining a substantially constant fluid pressure inside the distensible organ between about 60 mm Hg and about 120 mm Hg.

According to another aspect of the present disclosure, a system can include an endoscope defining a channel therethrough and a surgical instrument received within the endoscope channel. The surgical instrument can include a channel therein for connection with a source of suction. A regulator can be coupled to the surgical instrument channel between the instrument channel and the source of suction to regulate an amount of suction applied through the instrument channel.

Additional aspects of the present disclosure will be apparent to those of ordinary skill in the art in view of the detailed description of various implementations, which is made with reference to the drawings, a brief description of which is provided below.

DETAILED DESCRIPTION

The present disclosure is directed to a method and a system for endoscopically resecting tissue in a distended organ. The system can include a valve that enables the impedance to the inflow of distention fluid through the system into the distended organ to be maintained substantially the same, even as surgical instruments are inserted and removed from the endoscope during the surgical procedure. Maintaining an even distention pressure can be beneficial to the patient in that it can help to reduce the risks of over distention and intravasation and help to keep the surgical procedure as short as possible.

Figure 1:
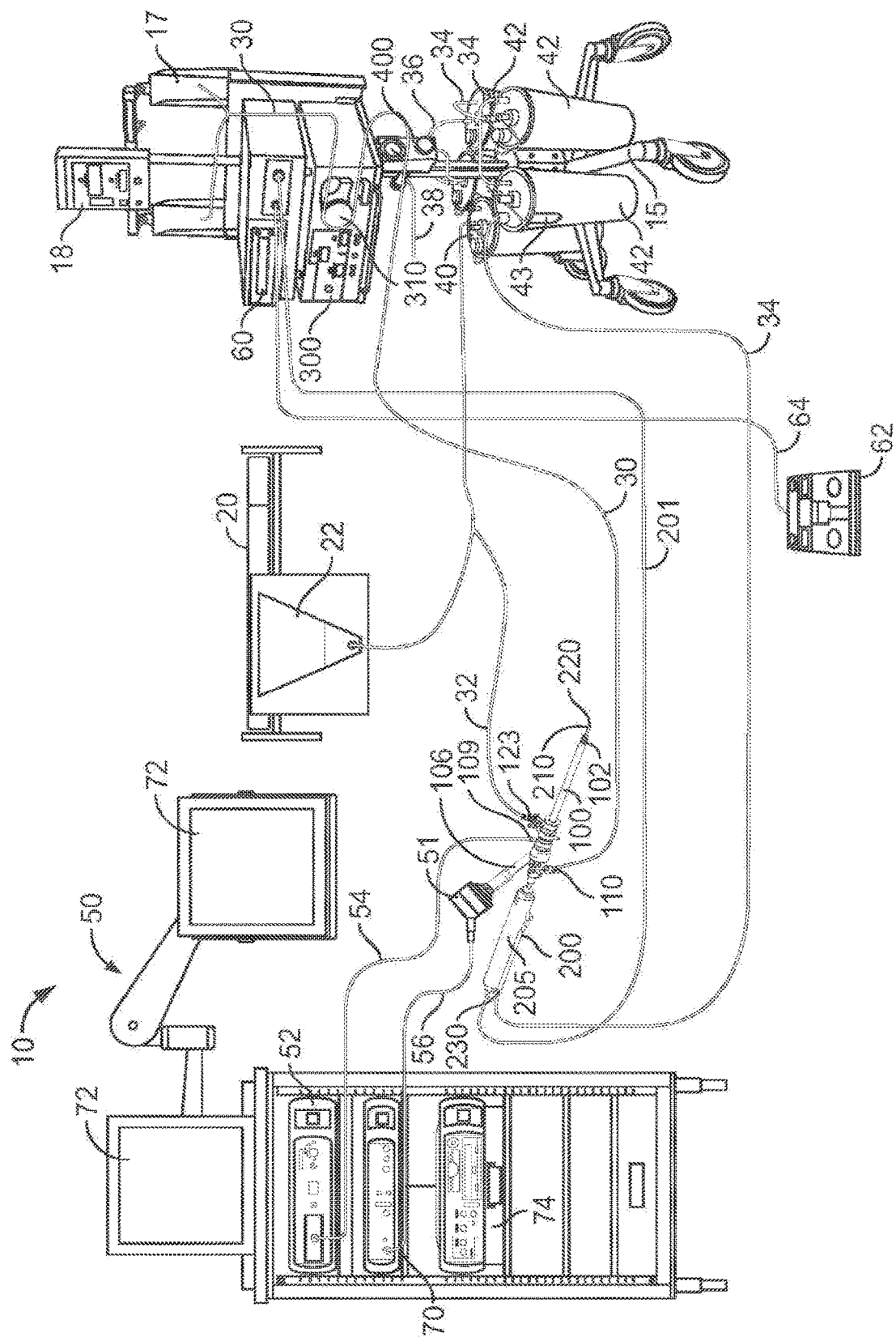
FIG. 1 shows a schematic diagram of a resection system according to some embodiments of the present disclosure.

Referring to FIG. 1, the illustrative embodiment of the tissue resecting system 10 according to some embodiments of the present disclosure includes an endoscope, e.g., hysteroscope 100, having a distal portion 102 insertable into a distensible organ, e.g., a uterus, of a patient 20 to flow fluid into and remove fluid from the organ. The hysteroscope 100 can be connectable to fluid bags 17 (mounted on a cart 15 by an inflow line 30 to deliver fluid to the hysteroscope 100. In accordance with some embodiments, the inflow line 30 runs through a pump, e.g., peristaltic pump 310, of a fluid management control unit 300 on cart 15. The fluid management control unit 300 and/or the Pump 310 control the pressure of the fluid delivered along inflow line 30 to hysteroscope 100. System 10 can also be connectable to a gravity container 40 on cart 15 connected by an outflow line 32 to an outflow port 105 on hysteroscope 100 to collect the outflow of fluid from hysteroscope 100, under the force of gravity. In accordance with some embodiments, the outflow line 32 is optionally connected to a surgical drape 22 to collect fluid from patient 20 in gravity container 40.

As shown in the illustrative embodiment, system 10 includes a resector 200 that can be received within hysteroscope 100 during use to resect tissue from the organ. The resector 200 in this embodiment includes a handle 205 and a distal portion 210 that extends out of distal portion 102 of hysteroscope 100. Distal portion 210 includes a working end 220, e.g., a morcellator that can be actuated to cut tissue from the organ. In this embodiment, handle 205 includes a motor (not shown) coupled to working end 220 to rotate working end 220 about a longitudinal axis to cut tissue. Also, optionally located on cart 15 is a resector control unit 60 of system 10 connected by a wire 64 to resector 200 to control movement of working end 220. In this embodiment, system 10 includes a foot-pedal 62 connected to control unit 60 by a wire 64 to actuate control unit 60.

Also, optionally located on cart 15 is one or more vacuum containers 42 of system 10 connected by suction line 34 to a suction port 230 on resector 200 to collect fluid and tissue suctioned through resector 200. In this embodiment, at least one of vacuum containers 42 includes a tissue trap 43 that collects tissue suctioned through suction lines 34 for later examination, e.g., by a pathologist. In this embodiment, system 10 also includes a vacuum regulator 400 connected by a suction line 36 to vacuum containers 42 and by vacuum line 38 to a vacuum source (not shown) to regulate suction provided by the vacuum source through suction channel 204 of resector 200.

Also, optionally located on cart 15 is a fluid monitoring unit 18 of system 10 that tracks the amount of fluid collected in gravity container 40 and vacuum containers 42 and the amount of fluid pumped by fluid management control unit 300 and can be configured to set off an audible and/or visual alarm if the difference between the amounts of fluid pumped and collected is above a threshold value, thus minimizing the possibility of excess fluid intravasation.

In this embodiment, part of system 10 includes a visualizing and imaging assembly 50 that includes a camera 51 coupled to a camera port 106 of hysteroscope 100, and a light source 52 coupled by a fiber optic cable 54 to a light port 109 of hysteroscope 100. Together, camera 50 and light source 52 allow a user to remotely visualize the tissue at distal end 102 of hysteroscope 100. In this embodiment, assembly 50 also includes an imaging station 70 connected by a fiber optic cable 56 to camera 50. Imaging station 70 includes one or more monitors 72 for viewing images from camera 50 and a capture system 74 for making a recording of the images.

Figure 2A:
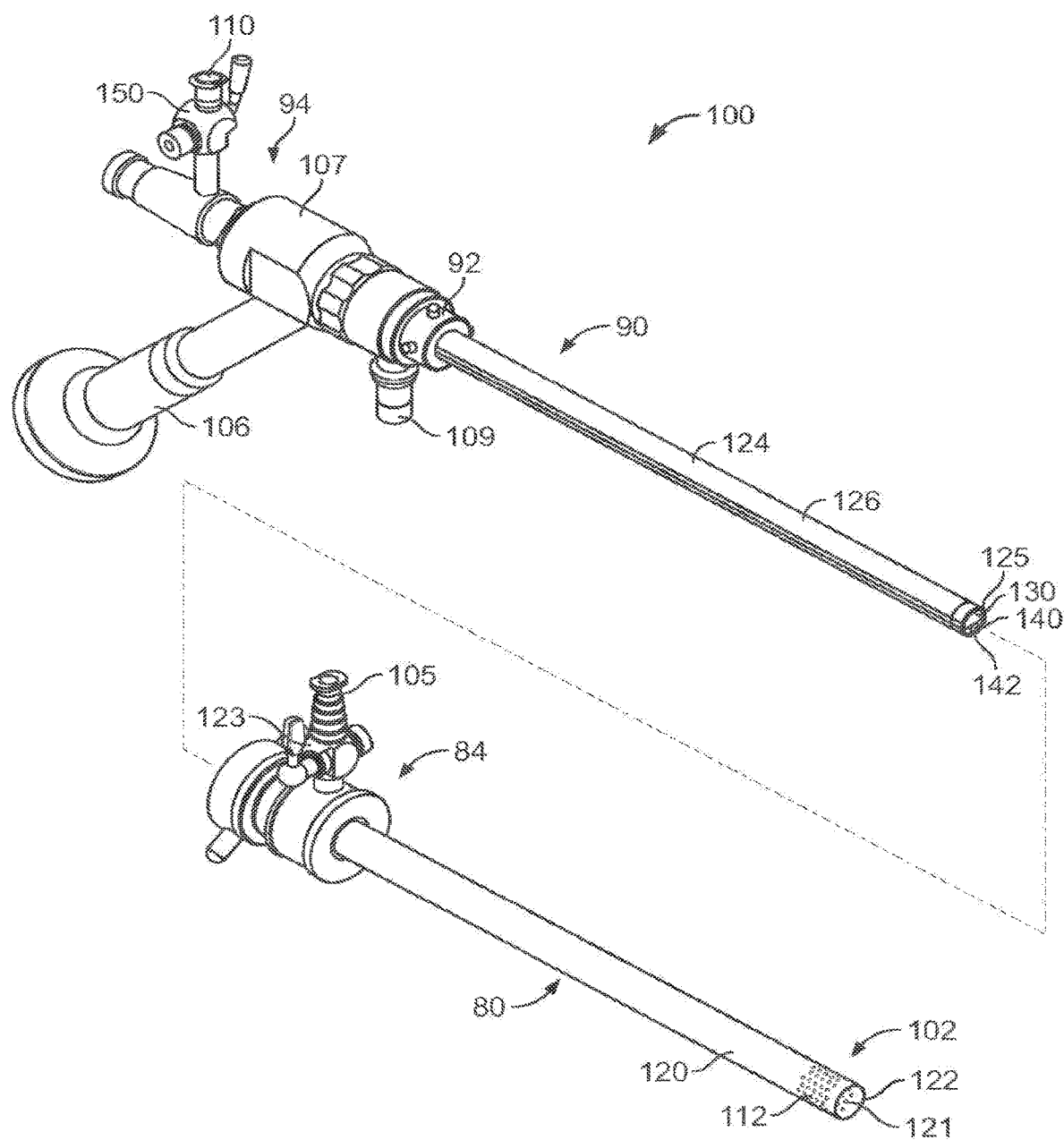
FIG. 2A shows an exploded, perspective view of a hysteroscope of the system of FIG. 1.
Figure 2B:
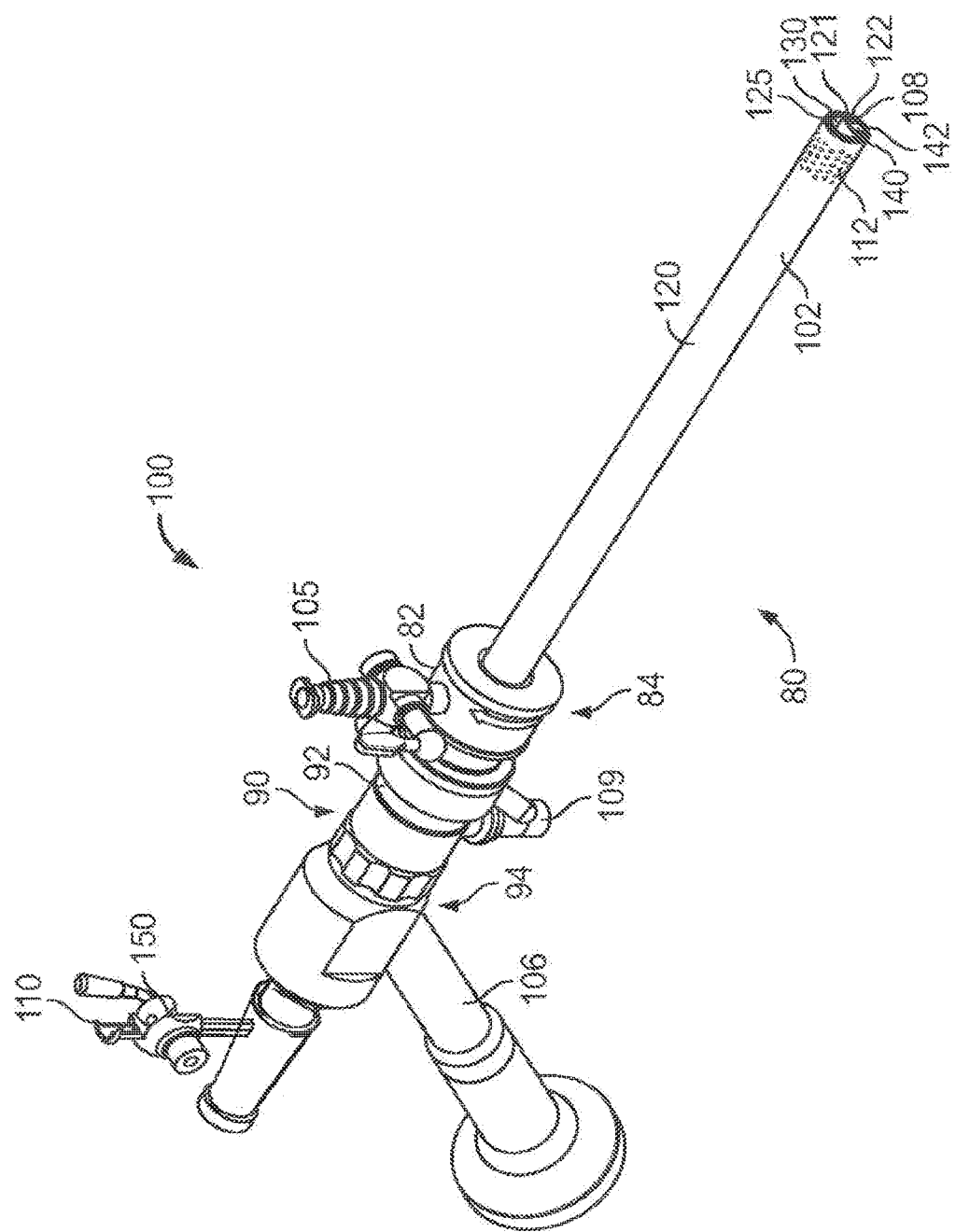
FIG. 2B shows a perspective view of the assembled hysteroscope of FIG. 2A.

Referring to FIGS. 2A and 2B, hysteroscope 100 optionally includes a sheath 80 that has a tube 120 with an inner wall 122 defining a channel 121 therethrough. In this embodiment, distal end 102 of tube 120 includes a plurality of holes 112 in communication with channel 121 for allowing fluid to flow out of an organ through channel 121. In this embodiment, sheath 80 has a proximal portion 84 that includes outflow port 105. In this embodiment, outflow port 105 is in fluid communication with channel 121. An on/off valve 123 is optionally positioned between outflow port 105 and channel 121 for turning on and off fluid flow from channel 121 to outflow port 105.

In this embodiment, hysteroscope 100 includes a scope housing 90 that has an elongated member 124 removably receivable in tube 120. Member 124 includes an outer wall 126 and an inner wall 125. In this embodiment, inner wall 125 defines an inflow channel 130. A proximal portion 94 of scope housing 90 includes inflow port 110, and a valve 150 which are fluidly connected to inflow channel 130, as described below. Member 124 also defines a lens channel 140 that houses an optical lens 142. Scope housing 90 includes a proximal portion 94 that includes camera port 106 and light port 109, which are coupled to optical lens 142 by fiber optic lines (not shown). Light travels from light port 109 to distal end 102 of hysteroscope 100 to illuminate objects near distal end 102. Light for images of those objects are received by optical lens 142, and travel through camera port 106 to camera (FIG. 1), to allow the user to view the organ through hysteroscope 100. This configuration enables lens channel 140 to be positioned adjacent to inflow channel 130 to help keep optical lens 142 clear of debris during use. Proximal portion 94 of scope housing 90 optionally includes a pin 92 receivable in a J-shaped slot (not shown) in sheath 80 to releasably lock scope housing 90 to sheath 80 when member 124 is received in tube 120.

Figure 3A:
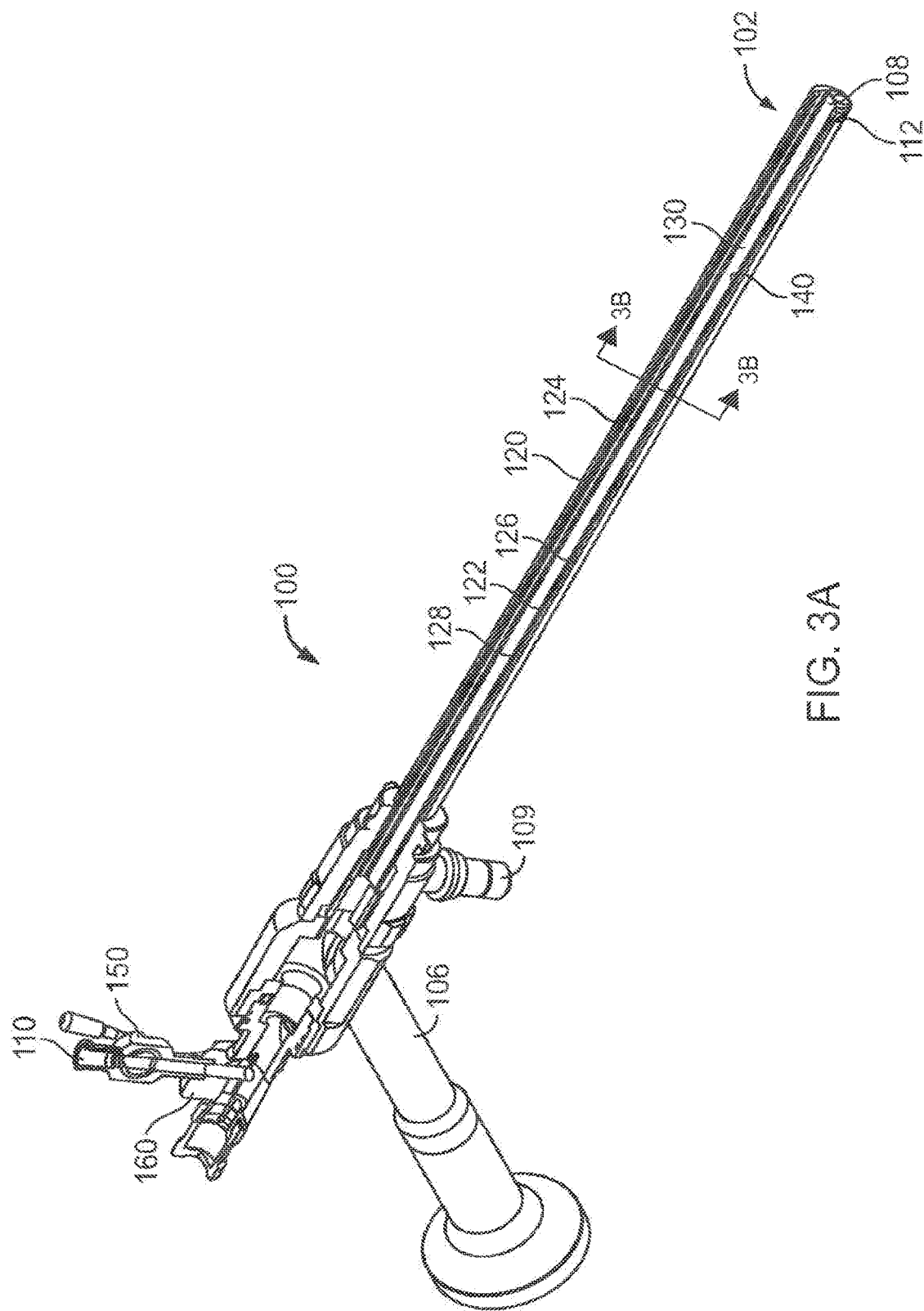
FIG. 3A shows a longitudinal cross-sectional view of the hysteroscope of FIG. 2B.
Figure 3B:
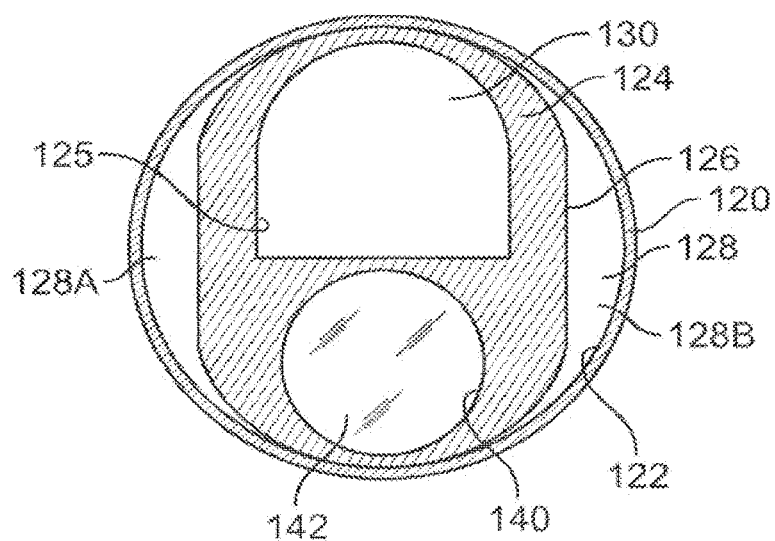
FIG. 3B shows a cross-sectional view of the hysteroscope of FIG. 2B taken along line 3B-3B.

Referring also to FIGS. 3A and 3B, when member 124 is received in tube 120, inner wall 122 of tube 120 and outer wall 126 of member 124 define a passive outflow channel 128 therebetween. Passive outflow channel 128 can be divided into a left portion 128A and a right portion 128B, which reconnect at outflow port 105. In this embodiment, passive outflow channel 128 is in fluid communication with holes 112 in distal end 102 of tube 120 and with outflow port 105 to permit passive outflow of fluid from the organ under the force of gravity. It will be understood that outflow channel 128 need not be divided. Inner wall 125 of member 124 defines inflow channel 130 in fluid communication with an aperture 108 in distal end 102 of hysteroscope 100 to permit fluid flow into the organ. Fluid can flow through passive outflow channel 128 along a path that is completely separate from a path along which fluid flows through inflow channel 130.

Referring to FIG. 3B, inflow channel 130 and passive outflow channel 128 can be sized and configured so that fluid management control unit 300, which has an inflow rate of up to 0.7 L/min, is able to maintain a substantially constant fluid pressure inside a distensible organ by pumping sufficient fluid into the organ through inflow channel 130 to balance fluid flow out of the organ through passive outflow channel 128, as described below. For example, inflow channel 130 can be configured to have a D-shaped cross-section with a cross-sectional area, e.g., of about 0.0153 to about 0.0461 square inches, preferably about 0.0307 square inches, and each portion 128A, 128B of passive outflow channel 128 can have a crescent-shaped cross-section with a combined cross-sectional area, e.g., of about 0.0083 to about 0.0249 square inches, preferably about 0.0166 square inches. It should be understood that other configurations and sizes of inflow channel 130 and passive outflow channel 128 can be used, so long as outflow of fluid through outflow channel 128 does not exceed the ability of fluid management control unit 300 to pump fluid into the organ through inflow channel 130 at least at the same flow rate as the outflow of fluid.

Figure 4:
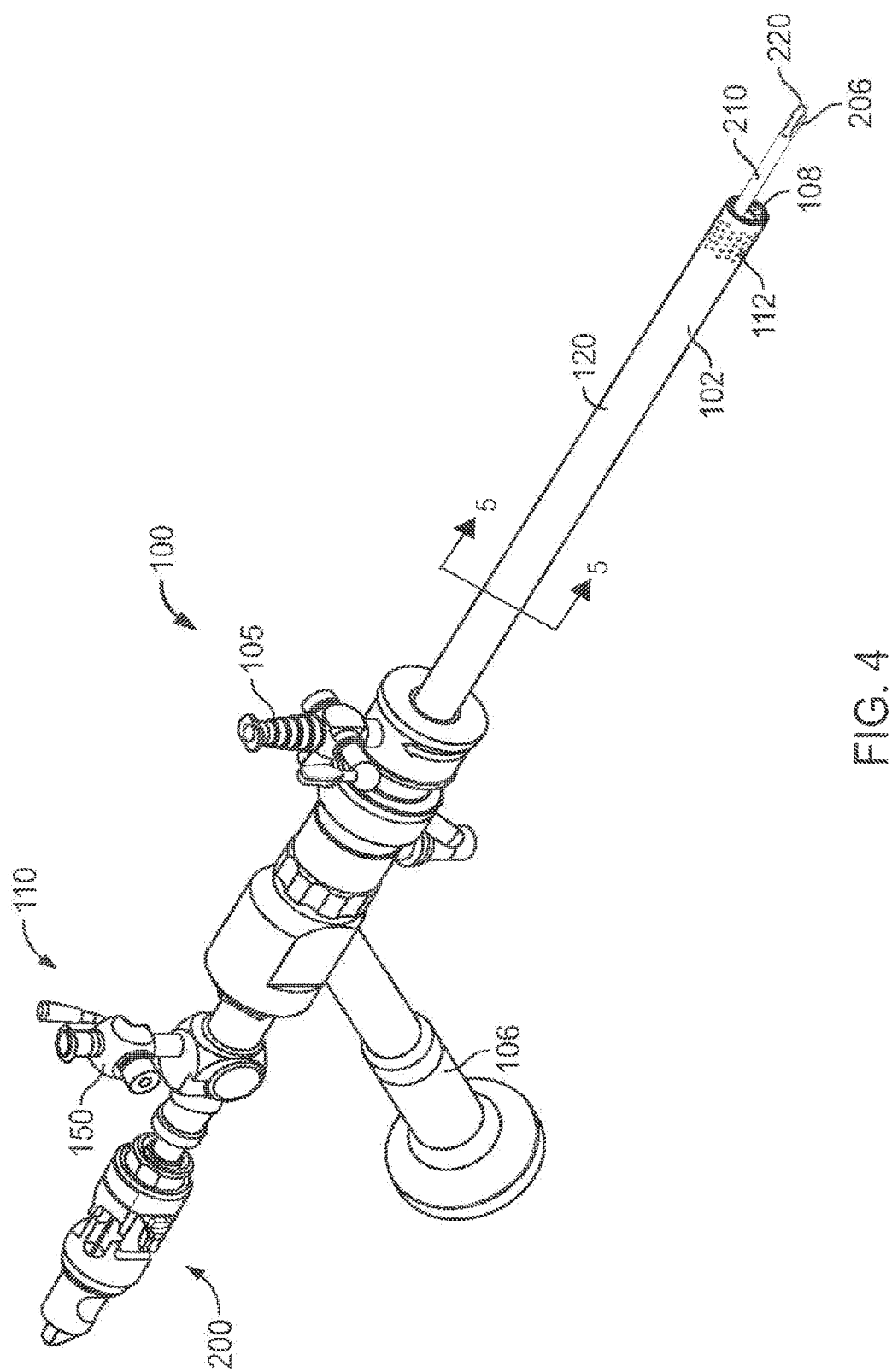
FIG. 4 shows a perspective view of the hysteroscope of FIG. 2B with a resector received therethrough.
Figure 5:
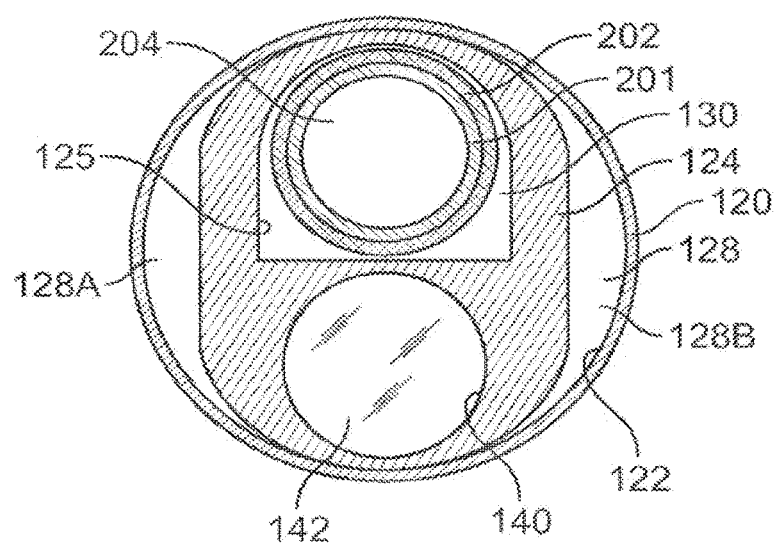
FIG. 5 shows a cross-sectional view of the hysteroscope and resector of FIG. 4 taken along line 5-5.

Referring to FIGS. 4 and 5, in this embodiment, resector 200 includes a stationary elongated outer tube 202 and a rotatable inner tube 201 that is coupled to working end 220 (not shown). Inflow channel 130 receives resector 200 therethrough. In this embodiment, the cross-section of inflow channel 130 is selected such that inflow channel 130 can be only partially blocked by resector 200, allowing fluid to continue to flow into the organ through a region of inflow channel 130 unblocked by resector 200, located between inner wall 125 and elongated tube 202. In this embodiment, inner tube 201 of resector 200 defines a suction channel 204 having an opening 206 at working end 220 of resector 200 and in fluid communication with suction port 230 of resector handle 205 (FIG. 1) to permit suction of fluid and tissue from the organ. Fluid is drawn through suction channel 204 along a path that is completely separate from the paths along which fluid flows through outflow channel 128 and inflow channel 130.

Referring to FIG. 5, passive outflow channel 128, inflow channel 130, and suction channel 204 can be sized and configured so that fluid management control unit 300 maintains the substantially constant fluid pressure inside the organ by pumping sufficient fluid into the organ to balance fluid flow out of the organ through passive outflow channel 128 and suction of fluid out of the organ through suction channel 204, as described below. For example, in this embodiment, the portion of inflow channel 130 not blocked by resector 200 has a cross-sectional area of about 0.0106 square inches, passive outflow channel 128 has a cross-sectional area of about 0.0166 square inches, and suction channel 204 has a cross-sectional area of about 0.0085 square inches. It should be understood that other configurations and sizes of inflow channel 130, passive outflow channel 128, and suction channel 204 can be used, so long as outflow of fluid through outflow channel 128 and suction of fluid through suction channel 204 do not exceed the ability of fluid management control unit 300 to pump fluid into the organ through inflow channel 130 at the same flow rate as the outflow of fluid.

Figure 14:
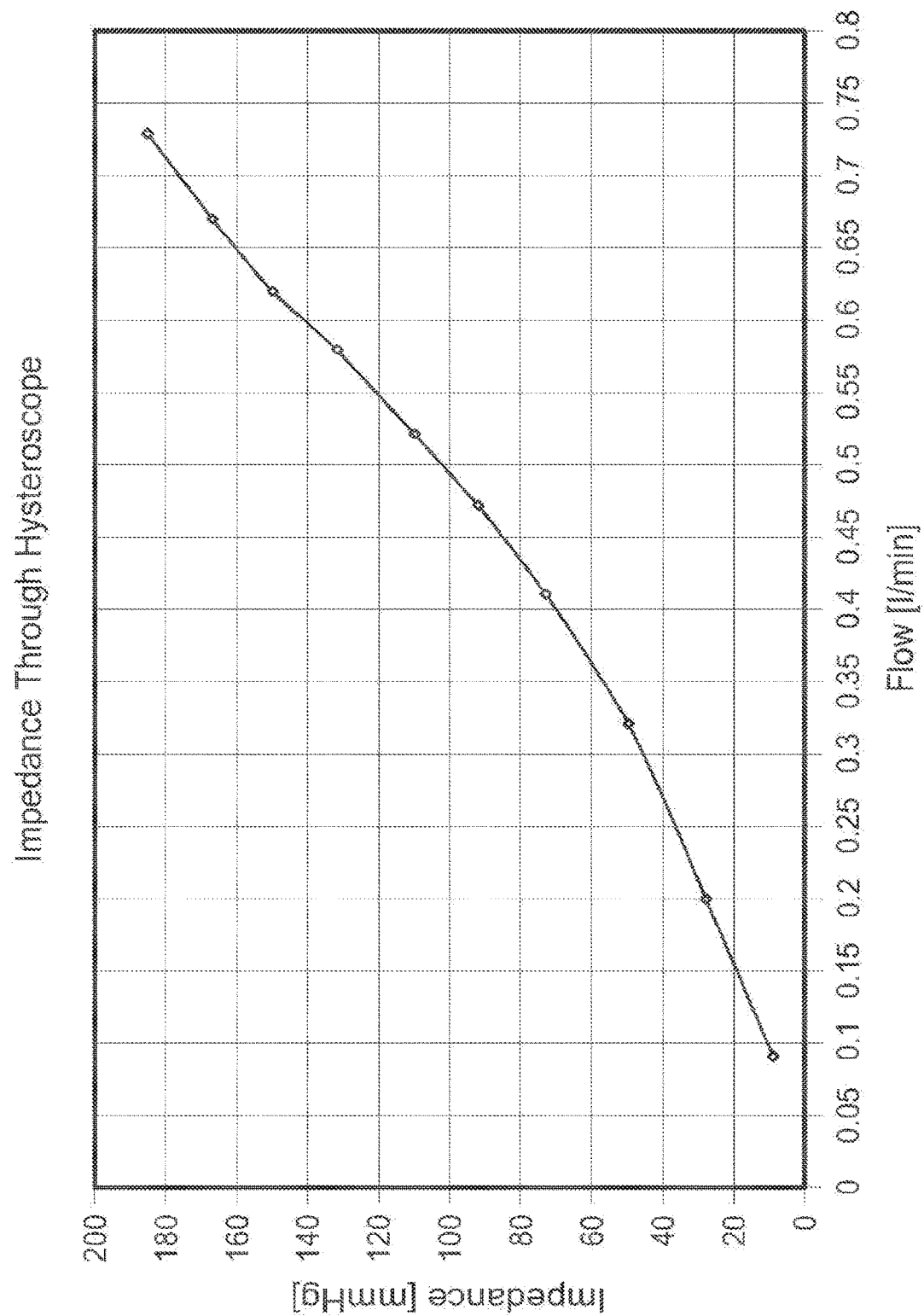
FIG. 14 shows a graph showing the impedance through the hysteroscope at various flow rates.

The ability of fluid management control unit 300 to maintain a substantially constant fluid pressure in the organ can be further facilitated by valve 150 of scope housing 90, which maintains substantially the same fluid flow impedance through inflow channel 130 regardless of whether resector 200 is positioned in scope housing 90. For example, FIG. 14 shows the impedance through hysteroscope 100 at various flow rates, regardless of whether resector 200 is positioned in scope housing 90. By maintaining a substantially constant fluid flow impedance, valve 150 facilitates fluid management control unit maintaining a substantially constant pressure in the organ regardless of whether resector 200 is positioned in scope housing 90. Impedance refers to the pressure drop in fluid between two points (in this case between inflow port 110 and the distal end of inflow channel 130) and varies proportional to the square of the flow rate.

Figure 6:
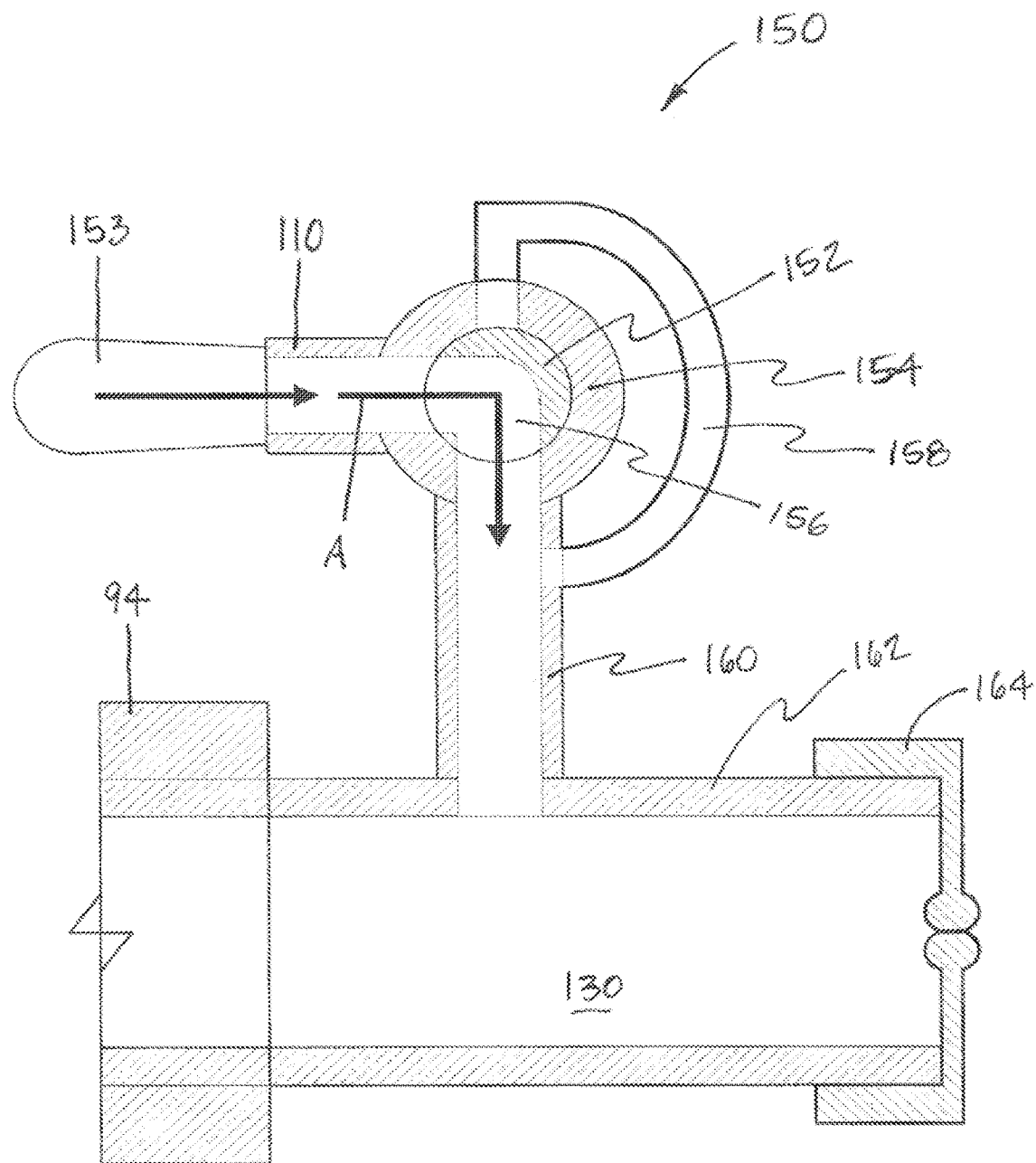
FIG. 6 shows a diagrammatic view of a valve in a first position according to some embodiments of the present disclosure.
Figure 7:
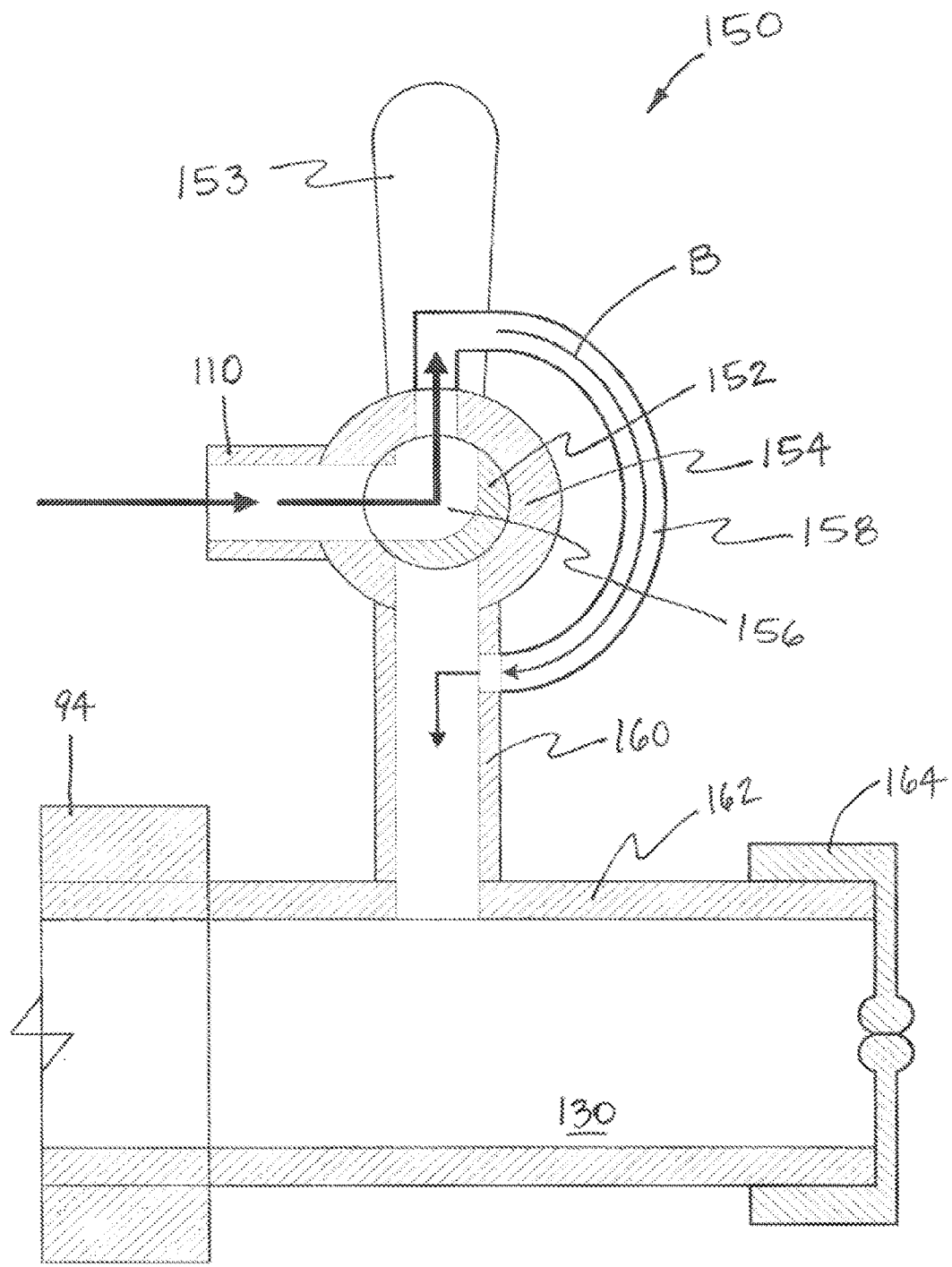
FIG. 7 shows a diagrammatic view of a valve in a second position according to some embodiments of the present disclosure.
Figure 8:
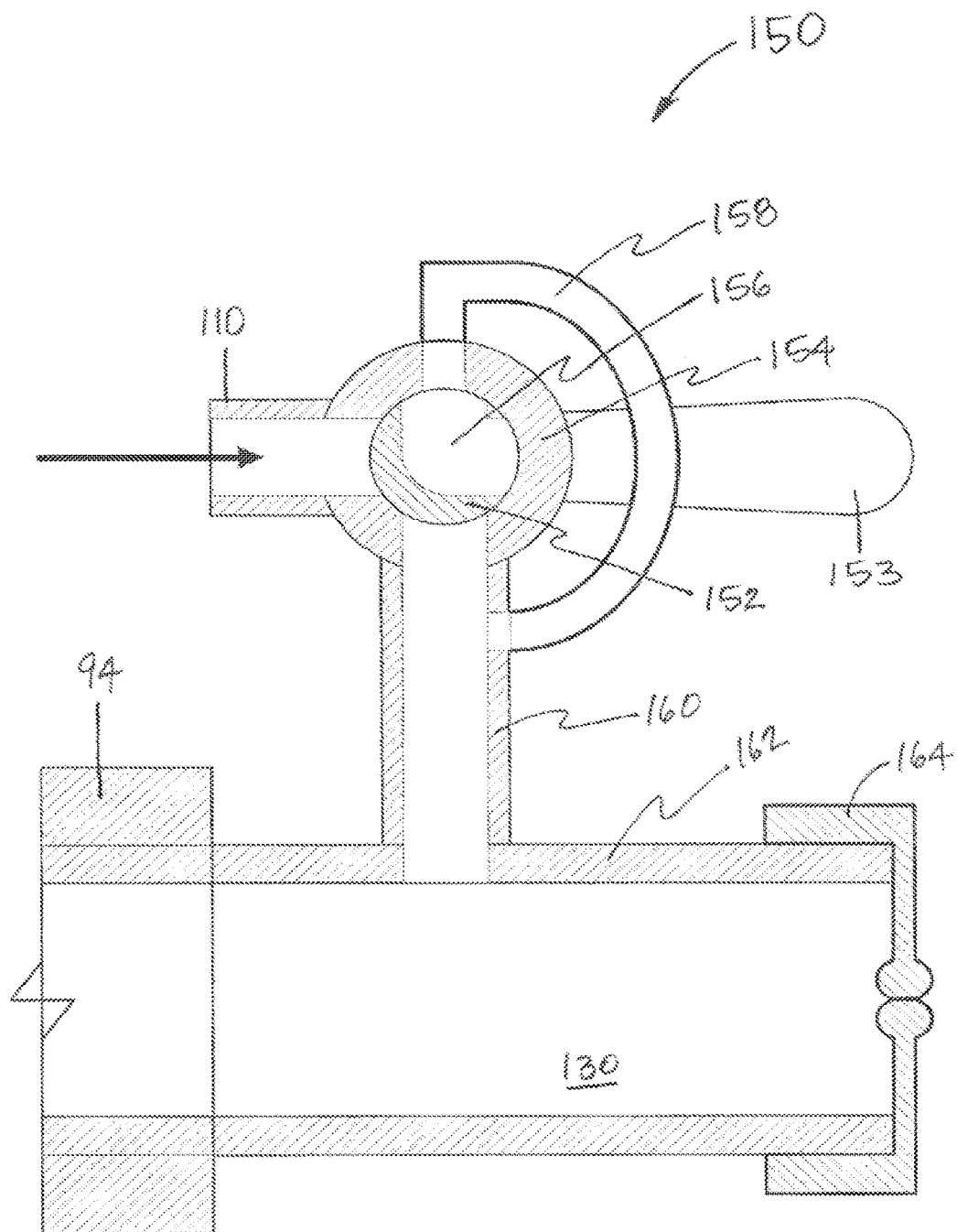
FIG. 8 shows a diagrammatic view of a valve in a third position according to some embodiments of the present disclosure.

FIGS. 6-8 show diagrammatic views of valve 150 located at the proximal end of the housing of the hysteroscope 100. In this embodiment, the valve 150 includes an inlet port 110 enabling the hysteroscope 100 to be connected to a source of fluid (not shown). In this embodiment, the valve 150 includes a valve body 152 that can rotate within the valve housing 154 to control the flow of fluid into the inflow channel 130. In this embodiment, the valve body 152 includes one or more channels 156 that connect one or more parts of the hysteroscope 100. In this embodiment, the valve body 152 includes a valve handle 153 to enable the user to move the valve body 152 between positions. In the first position, the valve body channel 156 connects the inlet port 110 to the channel 160 such that fluid supplied at the inlet port 110 flows through channel 160 into the inflow channel 130. In the second position, the valve body channel 156 connects the inlet port 110 to the calibration line 158. The calibration line 158 connects the valve body 154 to the channel 160 that is connected to the inflow channel 130. The calibration line 158 can be selected to have a predefined impedance to fluid flow that is substantially the same as the impedance to fluid flow when the valve body 152 is in the first position and the resector 200 is positioned in the inflow channel 130. In this embodiment, the impedance of the calibration line 158 is determined by the diameter of a portion of the calibration line or a flow restricting mechanism can be part of the calibration line 158. In accordance with some embodiments, the impedance of the calibration line 158 is, optionally, adjusted by adjusting the flow restricting mechanism or by replacing at least a portion of the calibration line 158 with a portion having a larger or smaller diameter. As shown in FIGS. 6-8, the inflow channel 130 extends proximally from the proximal portion 94 of the hysteroscope 100 and include an access port 162 into which the resector 200 can be inserted. In accordance with some embodiments, the access port 162 is optionally fitted with a seal 164 which allows the resector 200 to be inserted and removed and minimizes leakage of fluid through the access port 162. The seal 164 can be formed of an expandable material (e.g., rubber, silicone, PDMS) that can expand when the resector 200 is inserted in to the inflow channel 130, and contracts and remains closed after the resector 200 is removed. In accordance with some embodiments of the present disclosure, the access port 162 optionally includes a valve (not shown) that closes the proximal end of the inflow channel 130 when resector 200 is not present.

FIG. 6 shows a diagrammatic view of a valve 150 in a first position according to some embodiments of the present disclosure. In accordance with some embodiments of the present disclosure, the valve 150 in the first position is configured to allow the maximum fluid flow into the fluid flow channel. In the first position, the inlet port 110 is connected to channel 160 which directs fluid flow into the inlet channel 130. In this embodiment, the valve 150 provides the maximum flow and minimum impedance to fluid flow through the inlet channel 130.

FIG. 7 shows a diagrammatic view of a valve 150 in a second position according to some embodiments of the present disclosure. In accordance with some embodiments of the present disclosure, the valve 150 in the second position is configured to provide impeded fluid flow, at about the same impedance as when the resector 200 is inserted into the inflow flow channel 130. In the second position, the inlet port 110 is connected to calibration line 158 which directs fluid flow through the calibration line 158 and into the inlet channel 130. In this embodiment, the valve 150 provides calibrated fluid flow that matches the impedance to fluid flow when the resector 200 is received in the inflow channel 130. In operation, the user can place the valve 150 into the second position prior to inserting or removing the resector 200 to prevent a spike of excess fluid and pressure into the uterus during surgery. This reduces the risk of harm to the patient from intravasation.

FIG. 8 shows a diagrammatic view of a valve in a third position according to some embodiments of the present disclosure. In accordance with some embodiments of the present disclosure, the valve 150 in the third position can be configured to block fluid flow into channel 160 and the inflow channel 130 (e.g., this can be the "off" position). In the third position, the inlet port 110, calibration line 158 and channel 160 can each be closed by the valve body 152 such that no fluid can flow in the inlet port 110 or out via channel 160 or the calibration line 158.

Figure 9:
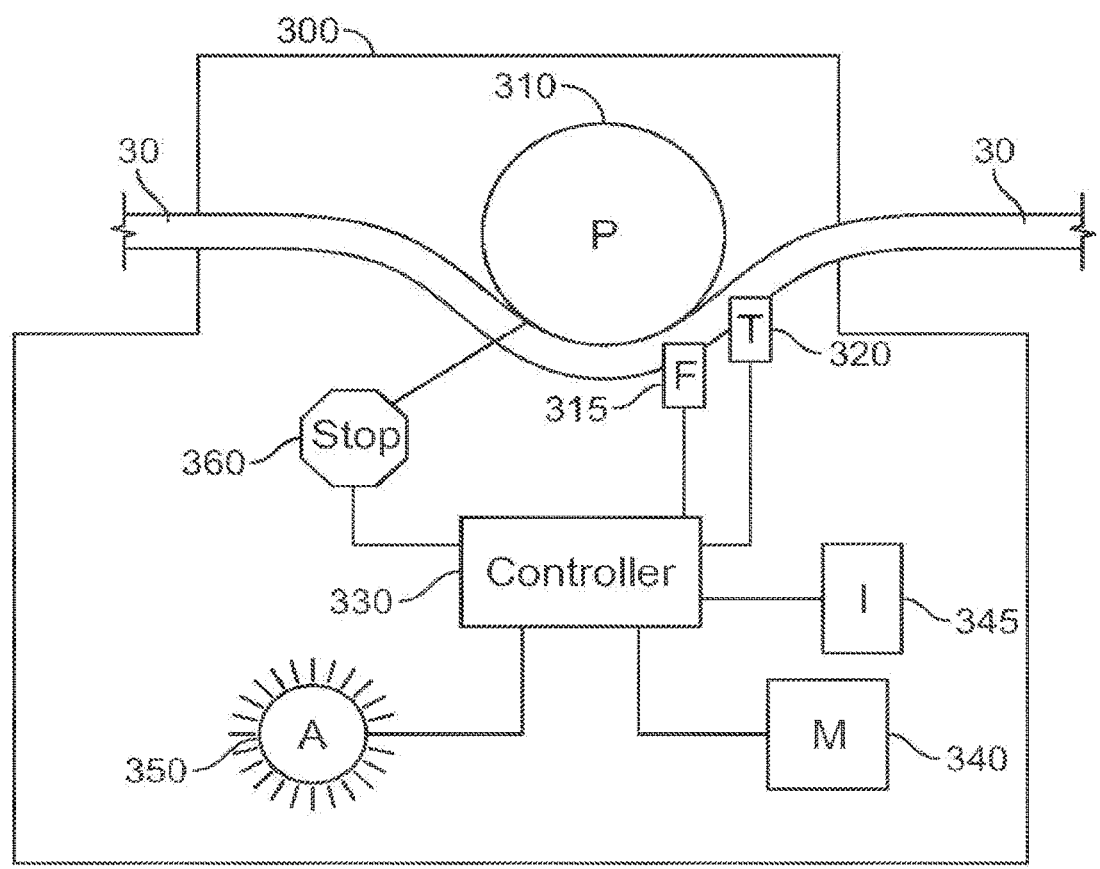
FIG. 9 shows a schematic diagram of a fluid management system of the resection system of FIG. 1.

In some embodiments of the present disclosure, fluid management control unit 300 is used to maintain substantially constant fluid pressure inside the organ by pumping sufficient fluid into the organ through inflow channel 130 to balance fluid flow out of the organ through passive outflow channel 128 and from suction of fluid through suction channel 204 (when resector 200 is received in hysteroscope 100). Referring to FIG. 9, fluid management control unit 300 optionally includes a peristaltic pump 310 through which runs fluid line 30 that transmits fluid from fluid bag 17 to inflow port 110 of hysteroscope 100. Pump 310 pumps fluid along fluid line 30, controlling the pressure and flow rate of fluid transmitted to hysteroscope 100.

Fluid management control unit 300 optionally also includes a flow rate sensor 315, such as a roller head, a turbine, or an ultrasonic sensor, that measures the flow rate of fluid outputted by pump 310. Control unit 300 optionally also includes a pressure sensor, e.g., pressure transducer 320 that senses the fluid pressure in fluid line 30 after the fluid passes through pump 310. In this embodiment, fluid management control unit 300 includes an input 345 where a user can input a desired pressure to be maintained inside the organ, and a memory 340 that contains information on the impedance (i.e., pressure drop) through the hysteroscope 100 and resector 200 combination at a range of different flow rates.

Coupled to pressure sensor 320, pump 310, flow rate sensor 315, input 345, and memory 340, is a controller 330, e.g., a microprocessor, that controls the pressure and the flow rate outputted by pump 310 based on the flow rate measured by flow rate sensor 315, the pressure measured by pressure sensor 320, the information stored in memory 340, and the target pressure 345. Based on a measured flow rate and a measured pressure, controller 330 determines the actual pressure in the organ according to the information stored in memory 340 that accounts for the impedance (i.e., pressure drop) through the hysteroscope 100 at various flow rates. Controller 330 then compares the pressure in the organ with the target pressure and adjusts the pressure and flow rate outputted by pump 310 accordingly. If the target pressure is greater than the actual pressure, then controller 330 increases the output of pump 310. If the target pressure is less than the actual pressure, then controller 330 decreases the output of pump 310.

The size and configuration of inflow channel 130, passive outflow channel 128, and suction channel 204 facilitate controller 330 maintaining substantially constant pressure in the organ. In addition, valve 150 facilitates maintaining a substantially constant pressure in the organ by keeping the impedance through hysteroscope 100 the same regardless of whether resector 200 is received in hysteroscope 100. Thus, it is not necessary for controller 330 to "know" whether resector 200 is positioned in hysteroscope 100. Fluid management control unit 300 is able to maintain a relatively constant pressure of fluid within the organ, e.g., at a preset pressure between about 60 mm Hg and about 120 mm Hg.

Fluid management control unit 300 can also include a feature that verifies that a correct combination of hysteroscope 100 and resector 200 is being used (i.e., to ensure that the system is only used when a resector and a hysteroscope having properly balanced flow channels are attached to fluid management control unit 300). Memory 340 contains flow rate and impedance information for each valid combination of a hysteroscope and a resector. Controller 330 is programmed to determine whether the pressure measured by pressure transducer 320 is within a threshold value of a predetermined pressure for a given flow rate in order to verify the identity of the combination of the hysteroscope and the resector. Controller 330 is coupled to a shut-off circuit 360 to disable pump 310 when controller 330 determines that the combination of hysteroscope and resector is invalid (e.g., when an incorrect size resector is used with the hysteroscope). If the combination is verified, then controller 330 overrides shut-off circuit 360 and allows pump 310 to pump fluid to hysteroscope 100, as described above. On the other hand, if controller 330 determines that the combination of the hysteroscope and the resector is invalid (e.g., wrong size resector), the controller 330 activates shut-off circuit 360 to disable pump 310. Controller 330 also is coupled to an alarm 350, e.g., a visual or audible alarm that is activated when pump 310 is disabled. Controller 330 is programmed to make pressure comparisons at several (e.g., three or four) flow rates prior to use of hysteroscope 100 and resector 200.

In use, a user can assemble the components of the resection system 10 as shown in FIG. 1. As shown in FIGS. 6 and 7, the user can position valve 150 to the first position. The user can insert the resector 200 through hysteroscope 100. The user can verify the combination of hysteroscope 100 and resector 200 by activating fluid management control unit 300, as described above with respect to FIG. 9, to infuse fluid through hysteroscope 100 and resector 200 assembly at three or four different flow rates, to sense the flow impedance through the assembly, and to compare each sensed flow impedance to predetermined flow impedances. If the combination is verified, the user removes resector 200 from hysteroscope 100, and moves valve 150 to the second position, as shown in FIG. 7.

Figure 10:
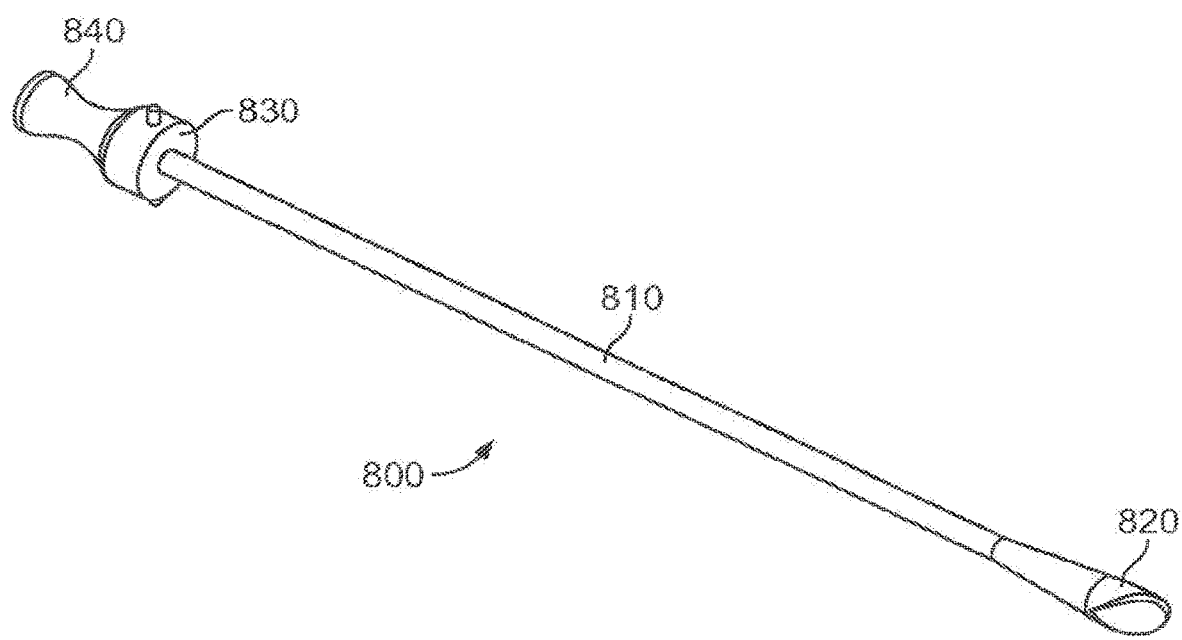
FIG. 10 shows a perspective view of an obturator for use with a sheath of the hysteroscope of FIG. 2A.

Referring to FIG. 10, to position sheath 80 within the uterus, system 10 includes an obturator 800 insertable through sheath 80 when scope housing 90 is removed from sheath 80. Obturator 800 includes a shaft 810, a sharp, distal tip 820, and a proximal handle 840. Disposed between handle 840 and shaft 810 is a pin 830 that fits into the J-shaped slot (not shown) in sheath 80 to removably lock obturator 800 to sheath 80.

Figure 11:
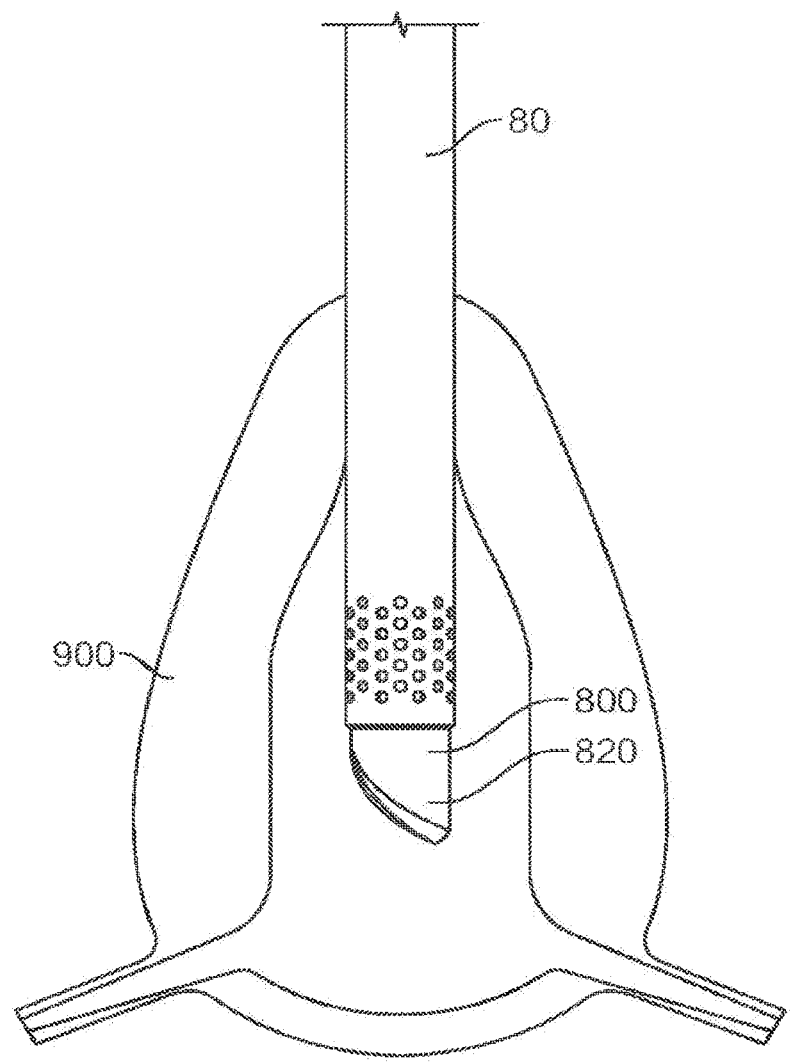
FIGS. 11-13 show the obturator, hysteroscope and resector in use.
Figure 12:
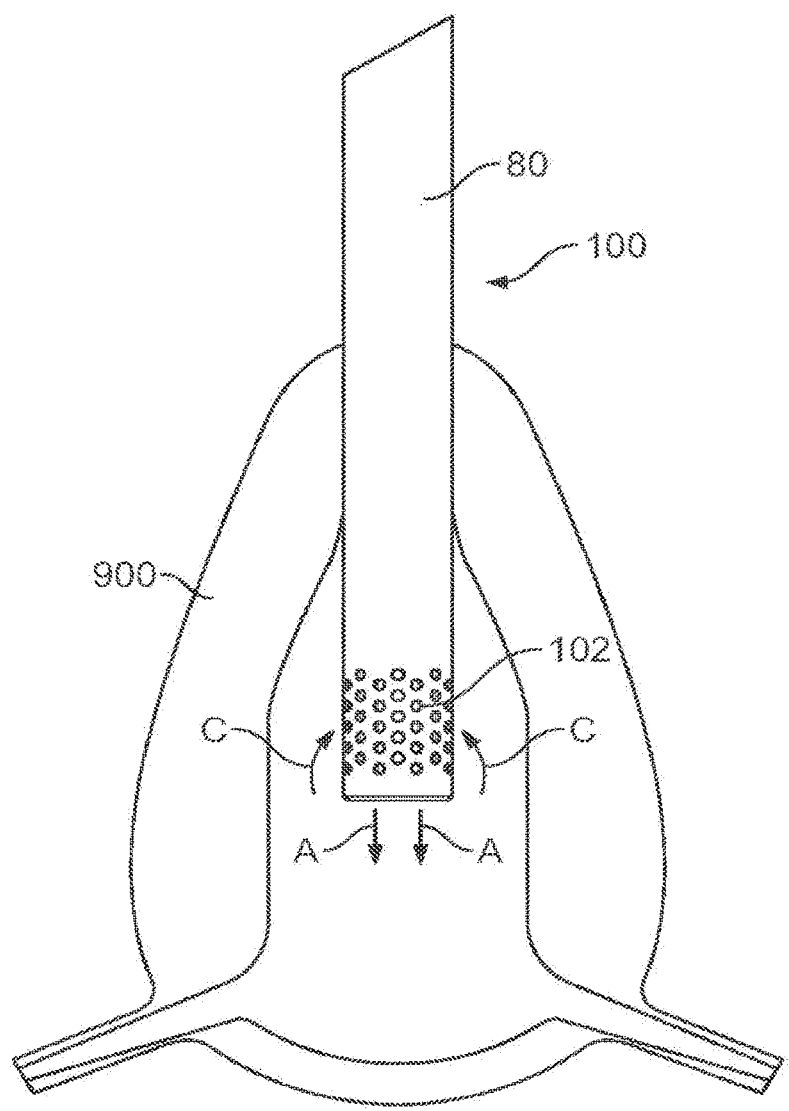

Referring to FIG. 11, with obturator 800 received within sheath 80 such that tip 820 extends beyond distal portion 102 of sheath 80, the user inserts obturator 800 and sheath 80 into a uterus 900. Referring to FIG. 12, the user removes obturator 800 from sheath 80, and inserts scope housing 90 through sheath 80 and into uterus 900. The user then moves valve 150 to the second position, as shown in FIG. 7, and activates fluid management control system 300 to pump fluid through channel 130 of hysteroscope 100 and into uterus 900 along flow path B, at a first impedance, to distend uterus 900, as shown in FIG. 12. At the same time, the user allows fluid to flow out of uterus 900 via holes 112 and channel 122 in hysteroscope 100 along flow path C to gravity container 40, in order to keep the pressure inside uterus 900 between about 60 mm Hg and 120 mm Hg.

Figure 13:
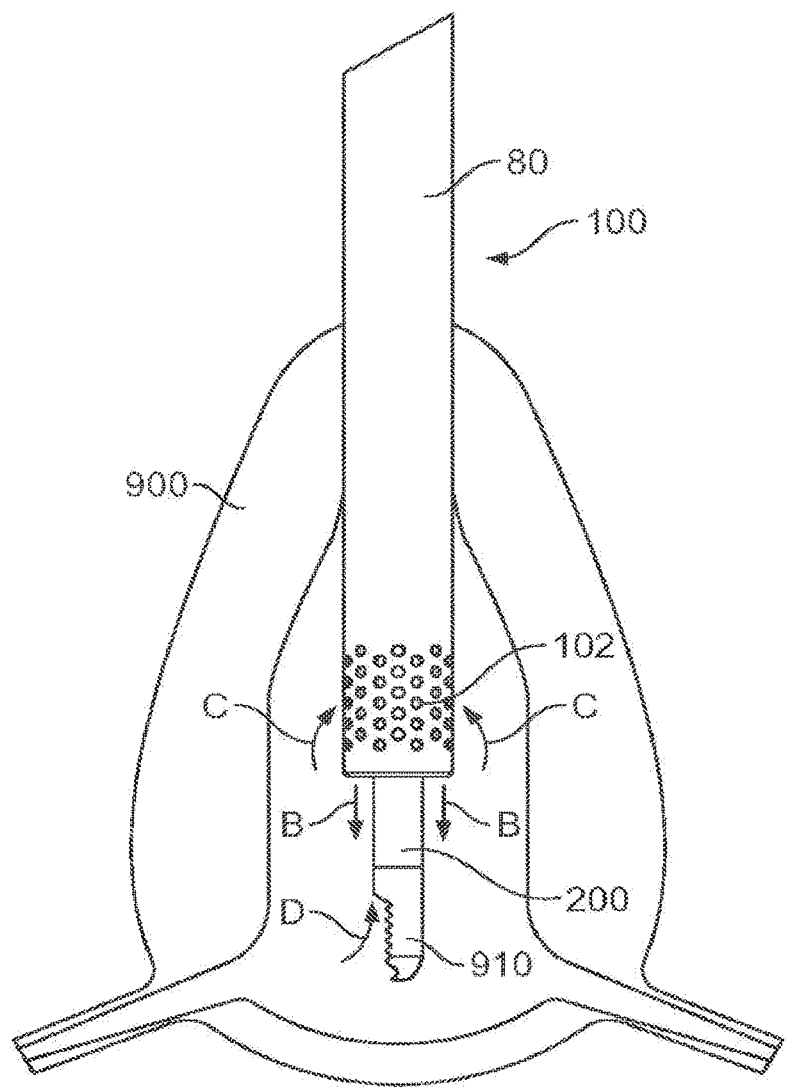

Once uterus 900 has been distended, with valve 150 in the second position, as shown in FIG. 7, the user inserts resector 200 through the access port 162 and inflow channel 130 of hysteroscope 100, and into uterus 900, as shown in FIG. 13 and positions valve 150 to the first position, as shown in FIG. 6. Fluid management control system 300 continues to pump fluid so that fluid flows through inflow channel 130, between inner wall 125 and resector 200 and into uterus 900 at a second impedance substantially equal to the first impedance. At the same time, the user allows fluid to flow out of uterus 900 via holes 112 and channel 128 in hysteroscope along flow path C and suctions fluid out of uterus 900 through resector 200 along flow path D, in order to keep the pressure inside uterus 900 between about 60 mm Hg and 120 mm Hg. Fluid suctioned along path D is collected in vacuum containers 42. The user also can actuate vacuum regulator 400 to control the amount of suction through resector 200 along path D. Preferably, the user maintains the vacuum pressure above approximately 100 mm Hg (to facilitate tissue removal) and below approximately 200 mm Hg (to inhibit uterus collapse). In order to inhibit uterus collapse, vacuum regulator 400 is preset to not allow vacuum pressure greater than a threshold value, e.g., 200 mm Hg, to be applied.

The user visualizes the inside of uterus 900 on monitors 72 of visualizing and imaging assembly 50. The user actuates foot pedal 62, which activates resector control unit 60. Resector control unit 60 activates resector 200, e.g., by rotating a cutting blade 910 at working end 220 of resector 200, to cut tissue from uterus 900. Fluid and tissue cut by blade 910 are suctioned through channel 204 of resector 200 along path D. During the procedure, resector 200 can be removed from hysteroscope 100 while hysteroscope 100 remains inside uterus 900, e.g., to clean resector 200 or change instruments, so long as the user moves valve 150 to the second position, as shown in FIG. 7, while removing resector 200 to limit the inflow of fluid through channel 130 of hysteroscope 100.

During the procedure, fluid monitor unit 18 can track the amount of fluid infused through resector 200 and the amount of fluid collected in gravity container 40 and vacuum containers 42. Fluid monitor unit 18 can set off an audible or a visual alarm if substantially more fluid is infused than collected, which indicates that the patient is absorbing too much fluid. Once the procedure is complete, the user can close valve 150 by moving it to the third position, as shown in FIG. 8, and removing resector 200 and hysteroscope 100 from uterus 900.

A number of embodiments of the present disclosure have been described. Nevertheless, it will be understood that various modifications may be made without departing from the spirit and scope of the present disclosure. For example, the shape, size, and configuration of the fluid flow channels through the hysteroscope and the resector could be different than that shown and described, such as having an inflow channel with an elliptical, square, triangular, or trapezoidal cross-section. Instead of a blind bore, the body of the secondary valve could include a peripheral channel formed in an outer surface of the body. Instead of a secondary valve, the primary valve could be electronically controlled to maintain a constant impedance through the hysteroscope regardless of whether the resector is inserted through the hysteroscope. The hysteroscope can be used with other types of resector tools having rotatable working ends, such as burrs or drills. The hysteroscope also can be used with a resector tool having a reciprocating working end, such as the instrument disclosed in U.S. Pat. No. 7,510,563 entitled "Reciprocating rotary arthroscopic surgical instrument," the entirety of which is incorporated herein by reference. The fluid management system can include another type of pump, such as a centrifugal, piston, or diaphragm pump. The vacuum regulator could include a manually or electronically operable valve, a flow sensor, and/or a pressure gauge. The devices shown can be used for surgery on other distensible organs, such as a shoulder or knee joint. Different combinations of the components of the system could be used or components could be added or deleted. These and other embodiments are within the scope of the following claims.

Other embodiments are within the scope and spirit of the present disclosure. For example, due to the nature of software, functions described above can be implemented using software, hardware, firmware, hardwiring, or combinations of any of these. Features implementing functions may also be physically located at various positions, including being distributed such that portions of functions are implemented at different physical locations.

Each of the above concepts and obvious variations thereof is contemplated as falling within the spirit and scope of the claimed invention, which is set forth in the following claims.

What is claimed is:
1. A hysteroscope comprising:
an access port defining a fluid flow channel and configured to receive an instrument through the fluid flow channel;
a valve inlet configured to receive a fluid;
a valve housing operably coupled to the valve inlet;
a valve body defining a body channel, the valve body movable within the valve housing at least between a first open position and a second open position; and
a valve channel in fluid communication with the fluid flow channel of the access port;

wherein when the valve body is:
in the first open position, a first flow path provides a first impedance to fluid flow from the valve inlet through the body channel of the valve body and through a first opening in the valve housing to the fluid flow channel of the access port; and
in the second open position, a second flow path provides a second impedance to fluid flow from the valve inlet through the body channel of the valve body, through a second opening in the valve housing and through a calibration line to the fluid flow channel of the access port,
wherein fluid is prevented from flowing through the calibration line when the valve is in the first open position.

2. The hysteroscope according to claim 1, wherein a third impedance to flow is produced when an instrument is received within the fluid flow channel of the access port, wherein the third impedance is substantially the same as the second impedance when an instrument is not received within the fluid flow channel of the access port and the valve body is in the second open position.

3. The hysteroscope according to claim 1, wherein the valve body has a closed position wherein fluid flow is blocked from passing through the valve housing when the valve body is in the closed position.

4. The hysteroscope according to claim 1, further comprising a seal operably coupled to a proximal portion of the access port, the seal configured to reduce fluid flow out of the access port.

5. The hysteroscope according to claim 1, wherein a distal portion of the access port is disposed on a proximal portion of the hysteroscope.

6. The hysteroscope according to claim 1, further comprising the calibration line, wherein the calibration line defines a calibration channel in fluid communication with the second opening in the valve housing and the fluid flow channel of the access port.

7. The hysteroscope according to claim 1, wherein the valve inlet is configured to operably couple to a pump such that the pump causes fluid to flow through the fluid flow channel of the access port.

8. A surgical system comprising:
a hysteroscope including an access port operably coupled to the hysteroscope, the access port defining a fluid flow channel configured to receive an instrument through the fluid flow channel; and
a valve operably coupled to the hysteroscope, the valve including:
a valve inlet configured to receive a fluid;
a valve housing operably coupled to the valve inlet;
a valve body defining a body channel, the valve body movable within the valve housing at least between a first open position and a second open position; and
a valve channel in fluid communication with the fluid flow channel of the access port;
wherein when the valve body is:
in the first open position, a first flow path provides a first impedance to fluid flow from the valve inlet through the body channel of the valve body and through a first opening in the valve housing to the fluid flow channel of the access port; and
in the second open position, a second flow path provides a second impedance to fluid flow from the valve inlet through the body channel of the valve body, through a second opening in the valve housing and through a calibration line to the fluid flow channel of the access port,
wherein fluid is prevented from flowing through the calibration line when the valve is in the first open position.

9. The surgical system according to claim 8, wherein a third impedance to flow is produced when an instrument is received within the fluid flow channel of the access port, wherein the third impedance is substantially the same as the second impedance when an instrument is not received within the fluid flow channel of the access port and the valve body is in the second open position.

10. The surgical system according to claim 8, wherein the valve body has a closed position wherein fluid flow is blocked from passing through the valve housing when the valve body is in the closed position.

11. The surgical system according to claim 8, further comprising a seal operably coupled to a proximal portion of the access port, the seal configured to reduce fluid flow out of the access port.

12. The surgical system according to claim 8, wherein a distal portion of the access port is operably coupled to a proximal portion of the hysteroscope.

13. The surgical system according to claim 8, wherein the valve includes the calibration line and the calibration line defines a calibration channel in fluid communication with the second opening in the valve housing and the fluid flow channel of the access port.

14. The surgical system according to claim 8, further comprising a pump coupled to the valve inlet such that the pump causes fluid to flow through the fluid flow channel of the access port.

15. The surgical system according to claim 14, wherein the pump is programmed to cause fluid to flow through the fluid flow channel of the access port to maintain a substantially constant pressure of between about 60 mm Hg and about 120 mm Hg inside a distensible organ.

16. The surgical system according to claim 14, further comprising a sensor coupled to the pump to sense a flow impedance at a given flow rate and a controller coupled to the sensor and the pump to compare the flow impedance to a predetermined flow impedance for the given flow rate.

17. The surgical system according to claim 16, wherein the sensor is configured to identify an instrument positioned through the access port based on the sensed flow impedance.

* * * * *